(12) United States Patent
Wilson et al.

(10) Patent No.: US 6,536,045 B1
(45) Date of Patent: Mar. 25, 2003

(54) TEAR-OFF OPTICAL STACK HAVING PERIPHERAL SEAL MOUNT

(75) Inventors: Seth Wilson, San Juan Capistrano, CA (US); Stephen S. Wilson, San Juan Capistrano, CA (US); Bart Wilson, San Juan Capistrano, CA (US)

(73) Assignee: Racing Optics, San Clemente, CA (US)

(*) Notice: Subject to any disclaimer, the term of this patent is extended or adjusted under 35 U.S.C. 154(b) by 0 days.

(21) Appl. No.: 10/039,519

(22) Filed: Jan. 3, 2002

Related U.S. Application Data

(63) Continuation-in-part of application No. 09/449,318, filed on Nov. 24, 1999, now Pat. No. 6,388,813.

(51) Int. Cl.$^7$ ................................................. A61F 9/00
(52) U.S. Cl. ................................... 2/15; 2/424; 2/434
(58) Field of Search ........................... 2/9, 15, 424, 432, 2/434; 351/44, 47; 359/359, 630, 631

(56) References Cited

U.S. PATENT DOCUMENTS

| | | | | |
|---|---|---|---|---|
| 4,076,373 A | * | 2/1978 | Moretti | 350/61 |
| 4,138,746 A | * | 2/1979 | Bergmann | 2/424 |
| 4,716,601 A | * | 1/1988 | McNeal | 2/434 |
| 5,420,649 A | * | 5/1995 | Lewis | 351/43 |
| 5,592,698 A | * | 1/1997 | Woods | 2/424 |
| 5,671,483 A | * | 9/1997 | Reuber | 2/424 |
| 5,740,560 A | | 4/1998 | Muoio | |
| 6,085,358 A | * | 7/2000 | Cogan | 2/424 |

\* cited by examiner

*Primary Examiner*—John J. Calvert
*Assistant Examiner*—Katherine Moran
(74) *Attorney, Agent, or Firm*—Stetina Brunda Garred & Brucker

(57) ABSTRACT

An optical stack of laminated removable lens for affixing to a face shield is disclosed. The stack includes a plurality of superposed removable lens adhesively affixed to one another, wherein each of the removable lens is held to each successive lens with a clear uninterrupted adhesive layer interposed between each lens. Each of the lens has a removal tab portion on one end which does not have any adhesive layer on either side thereof. This allows the wearer of the face shield to quickly grasp the removal tab portion for removing the top lens and exposing a clean lens directly underneath. The bottom-most removable lens of the stack has a band of adhesive formed around the periphery thereof for attachment of the stack to the face shield. The band of adhesive forms a seal which eliminates any moisture from the interface between the bottom-most lens and the shield.

11 Claims, 3 Drawing Sheets

TEAR-OFF OPTICAL STACK HAVING PERIPHERAL SEAL MOUNT

CROSS-REFERENCE TO RELATED APPLICATIONS

This application is a continuation-in-part of U.S. application Ser. No. 09/449,318, now U.S. Pat. No. 6,388,813 entitled OPTICAL STACK OF LAMINATED REMOVABLE LENSES FOR FACE SHIELDS, WINDOWS AND DISPLAY filed Nov. 24, 1999, the entire contents of which are incorporated by reference herein.

STATEMENT RE: FEDERALLY SPONSORED RESEARCH/DEVELOPMENT (Not Applicable)

BACKGROUND OF THE INVENTION

The present invention generally relates to the field of eye protectors or face shields having a lens cover plate, and in particular to peripheral seal mounts for a tear-off stack of laminated removable lens covers adhered to face shields and the like.

It is common practice to wear face shields in environments where injury of the eyes or face may occur from contamination. For example, face shields are worn by physicians working in the operating room. They are sometimes worn by those playing games where injury to the eyes may occur. For example, in the game of Paint Ball contestants employ weapons that fire at one another pellets or balls of paint as ammunition. When a ball of paint strikes a participant, it becomes readily apparent that they have been hit by a "tell-tale" blotch of paint. Obviously, it is desirable for contestants to wear some form of protection over their face and eyes.

In such environments as the Paint Ball game or the operating room, it is most likely that any face protection lens being worn will become covered with contaminants, which obscures the view. The solution would appear to be to simply clean off the lens. This is not always an option, especially for a physician performing an operation who cannot stop for such cleaning. An example of a recent solution to a similar problem is the use of a multi-ply transparent lens over goggles in order to facilitate rapid removal of dirt or grime in contaminated environments. That is, when the goggles become contaminated, a single layer of the multi-ply transparent lens is removed. The goggles are now clean and when they again become contaminated another layer of the multi-ply transparent lens is removed. This process can be repeated many times, depending upon the number of layers applied to the goggles. An example of this process and the materials used is disclosed in our application Ser. No. 09/449,318 filed Nov. 24, 1999 now U.S. Pat. No. 6,388,813 entitled OPTICAL STACK OF LAMINATED REMOVABLE LENSES FOR FACE SHIELDS, WINDOWS, AND DISPLAYS. The disclosure of which is expressly incorporated herein by reference.

In our above-cited patent, the problem we overcame was caused by reduced visibility as a result of the additive effect of the optical index of refraction for each layer applied. We overcame this problem by eliminating the air space between each successive layer of the multi-ply transparent lens and by inserting an adhesive layer between each lens layer. Thus, we created an adhesively laminated multi-layered clear film adapted to be used on a wearer's goggles, face shield or the like. However, when this same film is used for large area face protectors other problems arise. For example, when the bottom-most layer is adhered directly to the lens bubbles will appear, which bubbles are not easily removed because of the multi-layers over the bottom-most layer. Moreover, if the adhesive is omitted from the bottom-most layer, then we are back to the original refraction problem of an air gap between the eye-protector lens and the bottom-most layer of the multi-ply transparent lens. In addition, if the adhesive layer is removed from the interface between the bottom-most layer of the multi-ply stack and the lens of the face protector, then there remains the problem with the lens fogging up in the presence of moisture.

Accordingly, there is a need for a multi-ply transparent lens that will not produce bubbles when applied to the face protector's lens and will not reduce visibility due to a fogging up of the lens by moisture seeping into the interface between the bottom-most layer of the removable lens and the lens of the eye protector.

BRIEF SUMMARY OF THE INVENTION

Accordingly, a feature of the present invention is the use of selective areas of adhesive around the periphery of the bottom-most layer of a multi-ply transparent optical lens stack for attachment to a large area face protector. Preferably, the lenses and adhesive layers have an index of refraction between 1.40 and 1.52.

Another feature of the present invention is a method for the removal of a peripheral race around the edges of the bottom-most layer of a multi-ply transparent lens stack, thereby exposing adhesive around the periphery only. The peripheral adhesive area may then be used for affixing the multi-layer transparent lens to the face protector. Thus, the central area of the bottom-most layer of the multi-ply transparent lens remains in place, thereby avoiding the bubble problem. Also, the adhesive on the periphery solves the fogging up problem by sealing out any moisture.

Yet another feature of the present invention is an alternate method of forming the adhesive strip by applying a thin strip of adhesive directly to the bottom-most lens of the optical stack around the periphery thereof.

Still another feature of the present invention is the provision of an optical stack of removable lenses that may be used for windshields of vehicles, windows of all types, or video displays.

These and other features, which will become apparent as the invention is described in detail below, are provided by an optical stack of laminated removable lenses that may be affixed to a face shield. The stack includes a plurality of superposed removable lenses adhesively affixed to one another, wherein each of the removable lenses is held to each successive lens with a clear uninterrupted adhesive layer interposed between each lens. Each of the lens has a removal tab portion on one end which does not have any adhesive layer on either side thereof. This allows the wearer of the face shield to quickly grasp the removal tab portion for removing the top lens and exposing a clean lens directly underneath. The bottom-most removable lens of the stack has a band of adhesive formed around the periphery thereof for attachment of the stack to the face shield. The band of adhesive forms a seal which eliminates any moisture from the interface between the bottom-most lens and the shield.

Still other features and advantages of the present invention will become readily apparent to those skilled in the art from the following detailed description, wherein is shown and described only the preferred embodiment of the invention, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive, and what is intended to be protected by Letters Patent is set forth in the appended claims.

BRIEF DESCRIPTION OF THE DRAWINGS

The general purpose of this invention, as well as a preferred mode of use, its objects and advantages will best be understood by reference to the following detailed description of an illustrative embodiment with reference to the accompanying drawings in which like reference numerals designate like parts throughout the figures thereof, wherein.

DETAILED DESCRIPTION OF THE INVENTION

Figure 1:
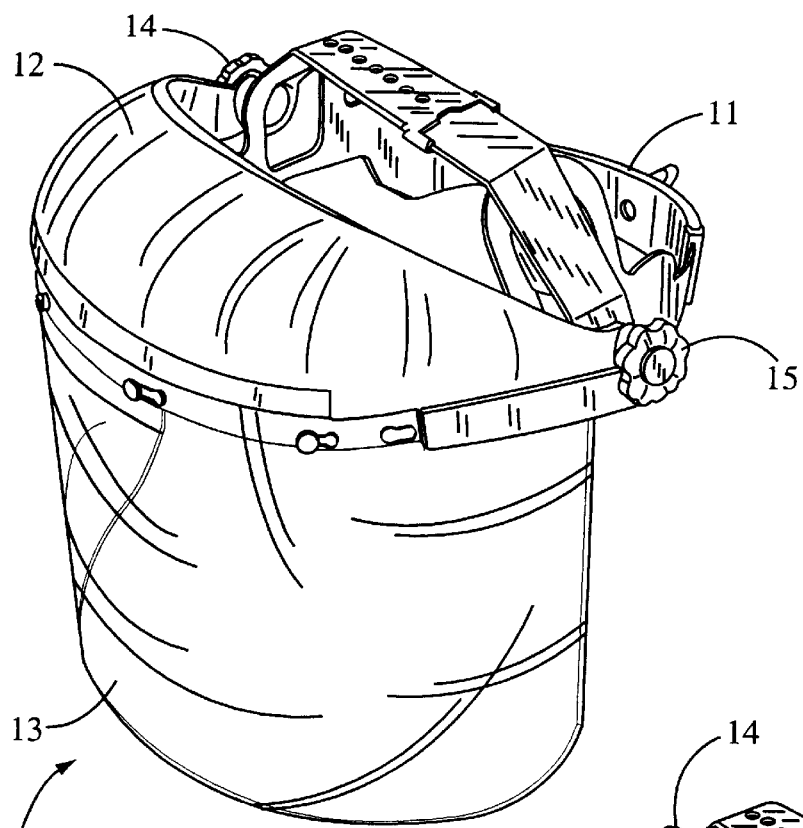
FIG. 1 is a perspective view of a face protector that may employ the multi-ply transparent lens stack according to the teachings of the present invention.

Referring now to the drawings and FIG. 1 in particular, a large area face protector 10 is shown in perspective view. The face protector may include an adjustable headband 11 and a frontal member 12 for supporting a lens 13. The frontal member 12 and lens 13 may be adjusted at an angle with the headband 11. Adjustment knobs 14 and 15 are available for holding the member 12 and lens 13 at the desired angle. Although a particular face protector is depicted, those skilled in the art will recognize that all face protectors, goggles and the like are contemplated for use in the present invention.

Figure 2:
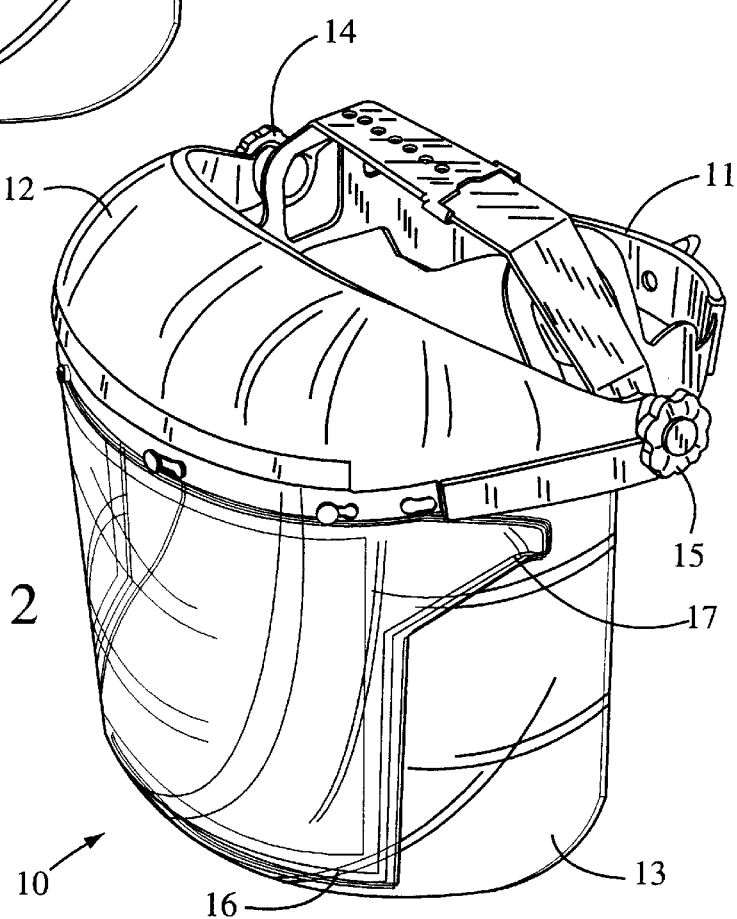
FIG. 2 is a perspective view of a face protector having attached thereto the multi-ply transparent optical stack according to the teachings of the present invention.

Referring now to FIG. 2, a perspective view of the face protector 10 is shown with a multi-ply transparent lens optical stack 16 attached thereto. The lens optical stack 16 is made and attached to the lens 13 according to the teachings of the present invention, amplified herein below. The lens optical stack 16 preferably includes tabs 17, which are employed by a wearer for removal of an individual layer of the lens optical stack 16. It is preferable that the removal tabs 17 do not have any adhesive on either side thereof so that a user will not pick up the adhesive on their fingers or gloves (if worn).

During use for example, when the lens optical stack 16 becomes contaminated and blocks the user's view, then one simply reaches up and grabs an individual tab 17 and peels off an outer layer of the lens optical stack 16. This process may be repeated as many times as there are layers in the lens optical stack 16.

Figure 3:
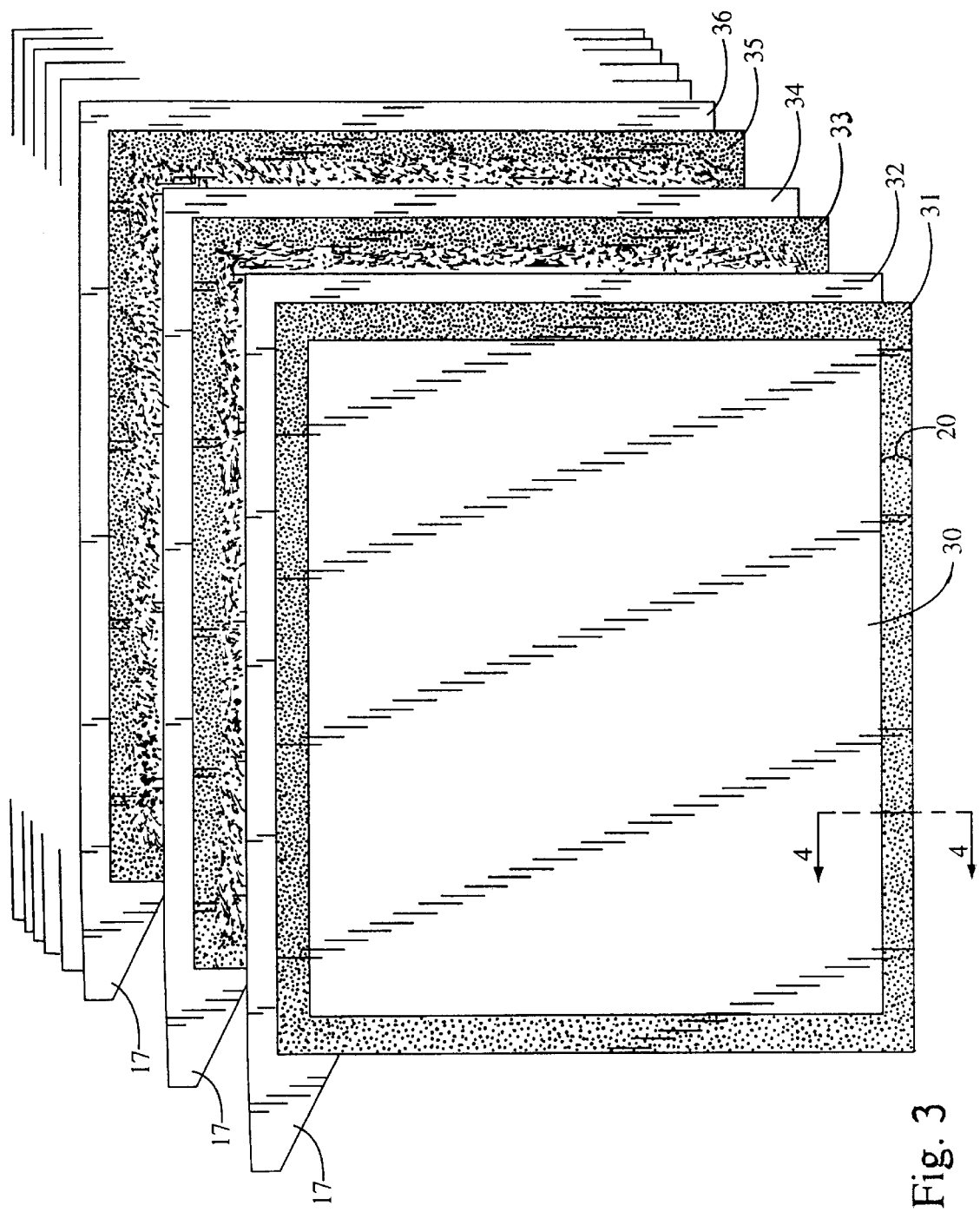
FIG. 3 is a partially exploded view of the multi-ply transparent optical stack showing the peripheral cut in the bottom-most layer, which cut exposes a periphery of adhesive for application to the face protector shown in FIG. 2.

Referring now to FIG. 3, a partially exploded view of the multi-ply transparent optical stack 16 is shown. This figure illustrates removable Mylar lenses or film layers 30, 32, 34, 36 . . . alternating with adhesive layers 31, 33, 35 . . . That is, the film layer 30 is held to the film layer 32 by the clear uninterrupted adhesive layer 31 interposed there between. The next film layer 34 is held to the film layer 32 by interposing the adhesive layer 33 there between, and so forth for formation of the entire lens optical stack 16.

The preferred material used to form the film layers 30, 32, 34, etc. is preferably a clear polyester. The layers are preferably fabricated from sheets of plastic film sold under the registered trademark Mylar owned by the DuPont Company and more particularly a type of Mylar made from a clear polymer polyethylene terephalate, commonly referred to as PET. Preferably, the lenses and clear adhesive layers have an index of refraction between 1.40 and 1.52. The preferred adhesive layers 31, 33, 35 etc. used to laminate the lenses together sequentially is a clear optical low tack material. The thickness of each film layer typically ranges from 0.5 mil to 7 mil (1 mil is 0.001"). The preferred thickness is 2 mil. Even after the adhesive material is applied to a 2 mil thickness layer, the thickness of the 2 mil thickness layer will still be 2 mil due to the adhesive film layer having only a nominal thickness. The term "wetting" can be used to describe the relationship between the laminated film layers. When viewing through the laminated layers, it appears to be one single piece of plastic film. No reflections are evident. The adhesive material 20 comprises a water based acrylic optically clear adhesive or an oil based clear adhesive, with the water based adhesive being the preferred embodiment. After the film layers 30, 32, 34 etc. are laminated or otherwise, bonded together with the interposed adhesive layers 31, 33, 35 etc., the thickness of each adhesive layer is negligible even though the adhesive layers are illustrated in as distinct layers. A preferred adhesive layer/film layer construction is disclosed in our pending application Ser. No. 09/449,318 filed Nov. 24, 1999 entitled Optical Stack of Laminated Removable Lenses for Face Shields, Windows, and Displays. The disclosure of which is expressly incorporated herein by reference. In accordance with a first embodiment of the present invention, a cut is made around the periphery of the bottom-most film layer 30, thereby exposing a narrow strip 20 of the adhesive layer 31. The strip 20 is used for adhesively affixing the optical stack 16 to the face protector 10. It is preferable to make the peripheral cut after the optical stack 16 is assembled into the multiple alternating layers in order to maintain proper registration of the individual layers. However, those skilled in the art will recognize the narrow strip 20 may be applied separately to the bottommost film layer 30 as well.

Figure 4:
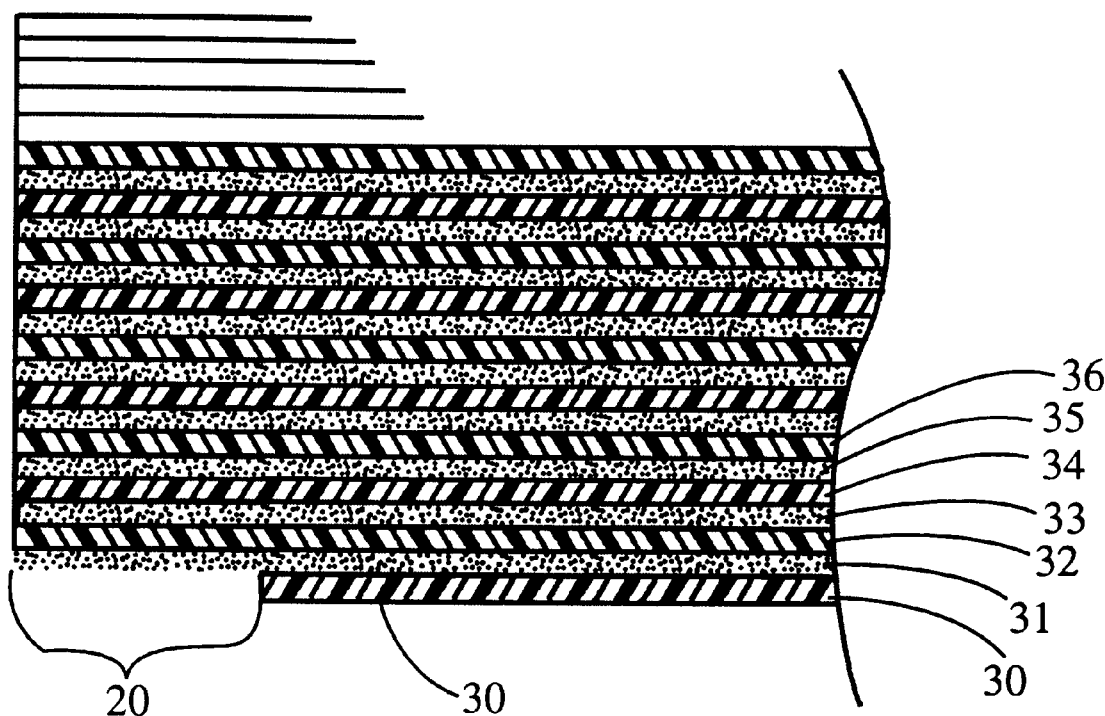
FIG. 4 is a partial cross-sectional view taken along line 4—4 in FIG. 3 showing a detail of the alternating film layers with adhesive layers between the film layers.

Referring now to FIG. 4, a partial cross-sectional view taken along line 4-4 of FIG. 3 illustrates a detail of alternating film layers 30, 32, 34, 36 . . . , with the adhesive layers 31, 33, 35, . . . interposed between each the film layers. It is noted that the peripheral cut exposing the strip 20 only removes a portion of the bottom-most film layer 30. This narrow peripheral strip 2- is preferably ⅛" to ½" in width, or wider. The more narrow the strip the more likely the stack will not stay in place on the face protector and the wider the strip the more likely the bubble problem, discussed above, will occur. Hence, I have discovered that the preferred width is as stated above, i.e., ⅛" to ½" in width.

As will be recognized, the multiply transparent optical stack 16 of the present invention can be easily applied to any desired face protector 10 by positioning the bottom-most film layer 30 having the narrow strip 20 of adhesive layer disposed about the periphery thereof adjacent to the front surface of the face protector. A user may then press the narrow strip 20 of the adhesive layer 31 against the outer surface of the face protector 10 causing the stack to be rapidly mounted thereto. In the preferred embodiment, the narrow strip 20 is attached to the face protector 10 adjacent one end thereof and subsequently spread or pressed tightly against the front surface of the face protector 10. In view of the large optical area of bottom-most film layer 30 being devoid of any adhesive, air bubbles or the like are not presented at the interface of the optical stack 16 and the face protector 10. However, because the optical stack 16 has adhesive layers there between, reflection between the film layers 30 is substantially reduced. During use, as unwanted material is splashed or presented to upper most film layer, the user may quickly remove the upper most film layer from the stack exposing a clean film layer there below. As such, it will be recognized that the present invention allows an effective optical stack to be rapidly deployed upon any optical surface and be rapidly used by a user.

Although the invention has been described with reference to a specific embodiment, this description is not meant to be construed in a limiting sense. Various modifications of the disclosed embodiment as well as alternative embodiments of the invention will become apparent to one skilled in the art upon reference to the description to the invention. It is therefore contemplated that the appended claims will cover any modifications of the embodiments that fall within the true scope of the invention.

What is claimed is:

1. An improved optical stack of laminated removable lenses for adhering to a face shield comprising:
   (a) a plurality of superposed removable lenses adhesively affixed to one another;
   (b) each said removable lens being held to each successive lens with a clear uninterrupted adhesive layer interposed between each said removable lens;
   (c) each said lens having a removal tab portion on at least one end which does not have any adhesive layer on either side of said tab portion for allowing the wearer of the face shield to quickly grasp said removal tab portion for removing the top lens and exposing a clean lens directly underneath said removed top lens; and,
   (d) the bottom-most removable lens of said stack having a band of adhesive formed around the periphery thereof for attachment of said stack to said face shield, wherein said band of adhesive forms a seal thereby eliminating any moisture from the interface between said bottom-most lens and said shield.

2. The optical stack as in claim 1 wherein said band of adhesive is formed by making a cut to the depth of the bottom-most lens, inside the periphery and contiguous to the lens shape, whereby the outer most generally annulus portion is then removed, thereby exposing the adhesive of the previous layer, which aids in mounting said lens to said face shield.

3. The optical stack as in claim 1 wherein said band of adhesive is applied to the periphery of said bottom-most lens.

4. The optical stack as in claim 1 wherein said removable lenses and said clear adhesive layers have an index of refraction between 1.40 and 1.52.

5. An optical stack of removable lenses for adhering to an optical window comprising:
   a) a plurality of generally rectangular superposed removable lenses adhesively adhered to one another so as to form said optical stack;
   b) each said removable lens being held to each successive lens with a clear uninterrupted adhesive layer interposed between each said removable lens;
   c) a plurality of staggered tabs extending from a corner of each of said film layers, said tabs being disposed to assist in allowing each film layer to be peeled off successively; and
   d) the bottom-most removable lens of said stack having a band of adhesive formed around the periphery thereof for attachment of said stack to said optical window, wherein said band of adhesive forms a seal thereby eliminating any moisture from the interface between said bottom-most lens and said optical window.

6. The optical stack as in claim 5 wherein said stack of removable lenses is adapted to be mounted on a windshield, window, face shield or a video display.

7. The optical stack as in claim 5 wherein said band of adhesive is formed by making a cut to the depth of the bottom-most lens, inside the periphery and contiguous to the lens shape, whereby the outer most generally annulus portion is then removed, thereby exposing the adhesive of the previous layer, which aids in mounting said lens to said optical window.

8. The optical stack as in claim 5 wherein said band of adhesive is applied to the periphery of said bottom-most lens.

9. The optical stack as in claim 5 wherein said removable lenses and said clear adhesive layers have an index of refraction between 1.40 and 1.52.

10. The optical stack as in claim 5 wherein said tabs do not have adhesive attached thereto.

11. A method for forming an optical lens stack for attachment to an optical window, said method comprising the steps of:
   a) laminating together a multiplicity of optical lens layers while interposing a clear uninterrupted adhesive layer between each optical lens layer being laminated;
   b) forming a tab extension from each optical lens layer and omitting said adhesive layer from said tab extension, whereby each of said lens layer may be peeled off individually; and,
   c) cutting around the perimeter and to a depth of one optical lens ply the bottom-most layer of said optical stack, thereby exposing a strip of adhesive for adhering said optical stack to said optical window.

* * * * *